United States Patent [19]

Leone-Bay

[11] Patent Number: 4,647,702

[45] Date of Patent: Mar. 3, 1987

[54] DEHYDROXYLATION OF ALPHA-HYDROXYKETONES

[75] Inventor: Andrea Leone-Bay, Ridgefield, Conn.

[73] Assignee: Stauffer Chemical Company, Westport, Conn.

[21] Appl. No.: 799,032

[22] Filed: Nov. 18, 1985

[51] Int. Cl.$^4$ .............................................. C07C 45/70
[52] U.S. Cl. .................................. 568/315; 568/347; 568/392; 568/13; 568/17; 568/322; 568/367; 568/404; 549/483
[58] Field of Search .................. 568/13, 17, 315, 347, 568/392, 322, 367, 404; 549/483

[56] References Cited

U.S. PATENT DOCUMENTS 3,011,000 11/1961 Garner ................................... 568/13
3,060,241 10/1962 Rauhut et al. ........................ 568/17
3,078,256 2/1963 Witteg et al. ........................ 568/17
3,099,691 7/1963 Rauhut et al. ........................ 568/17

OTHER PUBLICATIONS

Vedejs et al, J.A.C.S., vol. 93, pp. 4070–4072 (1971).
Cavazza et al, Tetrahedron Letters, vol. 23, pp. 4115–4118 (1982).
Vedejs et al, J. Org. Chem., vol. 38, pp. 1178–1183 (1973).

*Primary Examiner*—James H. Reamer
*Attorney, Agent, or Firm*—Hensley M. Flash

[57] ABSTRACT

A method for the dehydroxylation of alpha-hydroxyketone using lithium diphenylphosphide. The alpha-hydroxyketone, e.g. benzoin, is reacted with a solution of lithium diphenylphosphide followed by the addition of either an alkyl halide, e.g. methyliodide, or an alkyl halide and an organic acid, e.g. acetic acid, to yield the dehydroxylated compound, e.g. desoxybenzoin.

11 Claims, No Drawings

DEHYDROXYLATION OF ALPHA-HYDROXYKETONES

FIELD OF THE INVENTION

This invention relates to a process for the dehydroxylation of alpha-hydroxyketones, and particularly to a process using lithium diphenylphosphide.

BACKGROUND OF THE INVENTION

Related Information

Alkylated and methylene ketones are versatile synthetic intermediates useful in the manufacture of many chemicals that exhibit pharmaceutical, herbicidal and other activities. For example, methylisopropylketone ($Me_2CHCOMe$) is used to prepare the pesticide, 2,2-dimethyl-3-(2-halovinyl)cyclopropanecarboxylic acid esters and the antimycotic agents substituted 1,3-diazolyl-2-propanols while desoxyanisoin is used to prepare 4,5-bis(p-methoxyphenyl)-1,2,3-thiadiazole which exhibit activity as an inhibitor of collagen-induced aggregation of human platelet-rich plasma.

Heretofore, the two most commonly employed reagent combinations for dehydroxylation of alpha-hydroxyketones are red phosphorus/iodine and trimethylsilyliodide/sodium thiosulfate. Because of the versatility as synthetic intermediates of these dehydroxylated alpha-hydroxyketones, it would be advantageous to have other methods for preparing these compounds in good yields. It would be even more advantageous to have facile access to alpha-methylene ketones and alpha-alkylated ketones of the type $R_1C(O)CH_2R_2$ and $R_1C(O)CHR_2R_3$, respectively, by reduction of the corresponding alpha-hydroxyketones because these alpha-hydroxyketones are available in good yields by chlorotrimethylsilyl-mediated acyloin condensations of the appropriate esters. Further, the use of a readily available phosphorus derived reagent to accomplish this transformation would be advantageous.

Lithium diphenylphosphide (LDP) has been used as a reagent for the epoxide-mediated inversion of olefin stereochemistry. This reaction proceeds via stereospecific epoxide ring opening by LDP. The intermediate formed is treated with methyliodide effecting quaternization of phosphorus to give a betaine. Subsequent fragmentation of the betaine, usually at room temperature, produces an olefin and methyldiphenylphosphine oxide. This methodology has been employed to isomerize a variety of olefins via their epoxide derivatives, most notably, the conversion of cis- to trans-cyclooctene in greater than 90% yield with greater than 99.5% isomeric purity (see *Phosphorus Betaines Derived from Cycloheptane and Cyclooctene Oxides, Inversion of Cyclooctenes*, Vedejs, E.; Snoble, K. A. J.; Fuchs, P. L., *J. Org. Chem.* 1973, 38, 1178–1183).

SUMMARY OF THE INVENTION

An object of this invention is to provide a process for the dehydroxylation of alpha-hydroxyketones. A further object of this invention is to provide such a method using a readily available phosphorus-derived reagent, to accomplish this transformation.

Other objects and advantages of the present invention are shown throughout this specification.

In accordance with the present invention, a process for the dehydroxylation of an alpha-hydroxyketone has now been discovered comprising: (a) reacting an alpha-hydroxyketone with a solution of lithium diphenylphosphide, said solution being of a concentration sufficient to react with both the hydroxy and the ketone moieties to form an intermediate capable of further reaction with an alkyliodide; and (b) adding an alkyliodide to the reaction mixture of step (a) to form the corresponding alkylated ketone. The corresponding methylene ketone can be prepared by adding an organic acid with the alkyliodide to the reaction mixture of step (a). In this process the alpha-hydroxyketone is of the formula:

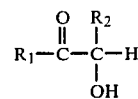

wherein $R_1$ and $R_2$ are the same or are different and are selected from the group consisting of a straight or branched chain alkyl having 1 to 10 carbon atoms, inclusive; cycloalkyl having 4 to 8 carbon atoms, inclusive; aryl and substituted aryl each having 6 to 12 ring carbon atoms, inclusive, wherein the substituents are selected from the group consisting of alkyl having 1 to 6 carbon atoms, inclusive, alkoxy having 1 to 6 carbon atoms, inclusive, and alkylene having 2 to 6 carbon atoms, inclusive; aromatic heterocyclic having 5 to 7 ring carbon atoms, inclusive, wherein the hetero-atom is selected from sulfur, nitrogen and oxygen; and $R_1$ and $R_2$ can together form a ring of up to 10 carbon atoms, inclusive, with the alpha-hydroxyketone moiety to which they are attached.

DETAILED DESCRIPTION OF THE INVENTION

The present invention comprises a process for dehydroxylating an alpha-hydroxyketone to either the corresponding alkylated or methylene ketone. In this process the alpha-hydroxyketone is of the formula:

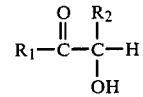

wherein $R_1$ and $R_2$ are the same or are different and are selected from the group consisting of a straight or branched chain alkyl having 1 to 10 carbon atoms, inclusive; cycloalkyl having 4 to 8 carbon atoms, inclusive; aryl and substituted aryl each having 6 to 12 ring carbon atoms, inclusive, wherein the substituents are selected from the group consisting of alkyl having 1 to 6 carbon atoms, inclusive, alkoxy having 1 to 6 carbon atoms, inclusive, and alkylene having 2 to 6 carbon atoms, inclusive; aromatic heterocyclic having 5 to 7 ring carbon atoms, inclusive, wherein the hetero-atom is selected from sulfur, nitrogen and oxygen; and $R_1$ and $R_2$ can together form a ring of up to 10 carbon atoms, inclusive, with the alpha-hydroxyketone moiety to which they are attached.

When either $R_1$ or $R_2$ is alkyl, an alkyl having 1 to 4 carbon atoms, inclusive, is preferred. When $R_1$ or $R_2$ is a cycloalkyl, a cycloalkyl having 5 to 6 carbon atoms, inclusive, is preferred. When $R_1$ or $R_2$ is an aryl or a substituted aryl, aryl and substituted aryl each having 6 ring carbon atoms are preferred. When $R_1$ or $R_2$ is a substituted aryl, the methoxy, the methyl, and the alkylene substituent having 3 to 4 carbon atoms, inclusive, are preferred. When $R_1$ or $R_2$ is an aromatic heterocyclic, 5 ring carbon atoms are preferred and sulfur or oxygen as the hetero-atom is preferred, with the most preferred aromatic hetero-cyclic being 5 ring carbon atoms with oxygen as the hetero-atom.

A proposed reaction mechanism for the process of this invention is represented by the equations below. However, these equations are only presented as aids in the discussion of this invention and it is not intended that the invention be limited thereby.

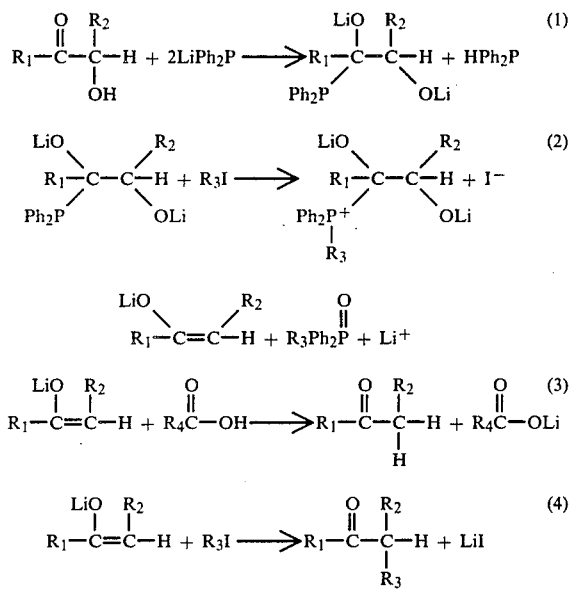

In the above reactions Ph designates a phenyl group.

In reaction (1) the alpha-hydroxyketone is reacted with two equivalents of LDP at room temperature. A reasonable mechanism can be envisioned that considers the initial deprotonation of the alpha-hydroxyl group by the first equivalent of LDP, followed by nuclophilic attachment of the second equivalent of LDP on the ketone carbonyl group to form a dianion. $R_1$ and $R_2$ are defined above.

In reaction (2) this dianion is reacted with an alkyliodide to yield an intermediate which undergoes elimination of methyldiphenylphosphine oxide through standard Wittig-type fragmentation. The concentration of LDP relative to the alpha-hydroxyketone in reaction (1) is important. Two equivalents of LDP are necessary to both deprotonate the alpha-hydroxyl group and attach to the ketone carbonyl group, thereby forming the dianion capable of undergoing reaction (2).

In reaction (2) $R_3$ is selected from the group consisting of a straight or branched chain alkyl having 1 to 6 carbon atoms, inclusive, with alkyl having 1 to 3 carbon atoms, inclusive, being preferred and methyliodide being particularly preferred.

The enolate formed after the elimination of alkyldiphenylphosphine oxide can further react with alkyliodide as in reaction (4) to obtain the corresponding alpha-alkylated ketone.

In reaction (3) the enolate is reacted with an organic acid to form the corresponding alpha-methylene ketone. Reactions (2) and (3) can proceed together to form the corresponding alpha-methylene ketone if the alkyliodide and the organic acid are added to the dianion at the same time. The reaction will proceed to the alpha-alkylated ketone if the alkyliodide is added in excess to the dianion in the absence of the organic acid.

In reaction (3) $R_4$ is selected from the group consisting of a straight or branched chain alkyl having 1 to 4 carbon atoms, inclusive, with acetic acid being preferred.

The versatility of the invention is demonstrated by the different end products resulting from reaction (3) and reaction (4). Either simple hydroxyl reduction or alkylative hydroxyl replacement is possible. Reaction of the dianion with excess alkyliodide gives the alpha-methylated ketone product, through overall replacement of the hydroxyl function by an alkyl group in one synthetic step. Whereas, in the presence of an organic acid, the dehydroxylated methylene ketone product results.

The molar ratio of the alpha-hydroxyketone to LDP can range from about 1:1.1 to about 1:4 with the preferred ratio being 1:2.

When an organic acid is added with the alkyliodide, the preferred ratio of the alkyliodide to the organic acid is 1:1.

The reactions of the present invention take place under atmospheric pressure in a nitrogen atmosphere.

The temperature range for these reactions can range from about 0° C. to about 50° C. with room temperature of about 25° C. being preferred. It is preferred that the alpha-hydroxyketone be added to the LDP, preferably dropwise, to maintain the temperature of the reaction medium close to room temperature of about 25° C. The LDP is bright orange and the reaction mixture goes to a pale yellow after addition of the alpha-hydroxyketone.

In a particularly preferred embodiment of this invention $R_1$ and $R_2$ are both phenyl, the alkyliodide is methyliodide and the organic acid is acetic acid.

The following Experiments describe various embodiments of this invention. Other embodiments will be apparent to one of ordinary skill in the art from a consideration of this specification or practice of the invention disclosed herein. It is intended that the specification and Experiments be considered as exemplary only, with the true scope and spirit of the invention being indicated by the claims which following the Experiments.

EXPERIMENTS

All reactions were conducted under a nitrogen atmosphere. In each case, the reaction products were characterized by comparison to authentic samples and found to be identical. The term MPLC refers to medium pressure liquid chromatography on a prepacked lobar column size C at 20 psi. Although LDP was prepared from lithium and diphenylphosphinouschloride, this reagent can also be made by treatment of diphenylphosphine with n-butyllithium. The following experimental procedure is representative of the dehydroxylation of alpha-hydroxyketones by use of lithium diphenylphosphide.

Dehydroxylation of Benzoin. Diphenylphosphinouschloride (5.0 g, 22.6 mmol) was added dropwise to a suspension of lithium shot (158 mg, 22.6 mmol) in THF (10 ml) at room temperature. After about 2 hours all the lithium had dissolved and a solution of benzoin (2.4 g, 11.3 mmol) in THF (25 ml) was added dropwise. The clear yellow reaction mixture was stirred overnight at room temperature and turned a bright orange color. Acetic acid (678 mg, 11.2 mmol) was then added, followed by methyliodide (1.6 g, 11.3 mmol). After stirring for an additional 30 minutes, the reaction mixture was poured into water (100 ml) and extracted with ethyl acetate. The combined organic extracts were dried over magnesium sulfate and concentrated in vacuo giving a yellow oil. MPLC purification on silica gel (eluting solvent, ethyl acetate) gave desoxybenzoin (1.7 g, 76 wt % yield) as a white crystalline solid.

Alpha-hydroxyketones of the formula

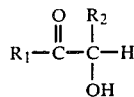

were subjected to dehydroxylation following procedures similar to that outlined above. The particular alpha-hydroxyketones used and the yield of the corresponding methylene ketone realized are listed in the following TABLE I.

TABLE I

| Run No. | $R_1$ | $R_2$ | Yield Wt % |
|---|---|---|---|
| 1 | p-OCH$_3$Ph | p-OCH$_3$Ph | 86 |
| 2 | CH$_3$ | i-propyl | 60 |
| 3 | (CH$_2$)$_{10}$ | | 72 |
| 4 | n-propyl | n-propyl | 52 |
| 5 | furan | furan | 81 |

In run No. 3, $R_1$ and $R_2$ formed a ring of 10 carbon atoms with the alpha-hydroxyketone moiety to which they are attached.

What is claimed is:

1. A process for the dehydroxylation of an alpha-hydroxyketone comprising:
   (a) reacting an alpha-hydroxyketone with a solution of lithium diphenylphosphide, said solution being of a concentration sufficient to react with both the hydroxy and the ketone moieties to form an intermediate capable of further reaction with an alkyliodide; and
   (b) adding an alkyliodide to the reaction mixture of step (a) to form the corresponding alkylated ketone.

2. The process of claim 1 wherein the alpha-hydroxyketone is of the formula:

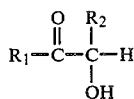

wherein $R_1$ and $R_2$ are the same or are different and are selected from the group consisting of a straight or branched chain alkyl having 1 to 10 carbon atoms, inclusive; cycloalkyl having 4 to 8 carbon atoms, inclusive; aryl and substituted aryl each having 6 to 12 ring carbon atoms, inclusive, wherein the substituents are selected from the group consisting of alkyl having 1 to 6 carbon atoms, inclusive, alkoxy having 1 to 6 carbon atoms, inclusive, and alkylene having 2 to 6 carbon atoms, inclusive; aromatic heterocyclic having 5 to 7 ring carbon atoms, inclusive, wherein the hetero-atom is selected from sulfur, nitrogen and oxygen; and $R_1$ and $R_2$ can together form a ring of up to 10 carbon atoms, inclusive, with the alpha-hydroxyketone moiety to which they are attached.

3. The process of claim 2 wherein $R_1$ and $R_2$ are both phenyl.

4. The process of claim 2 wherein the alkyliodide is methyliodide.

5. The process of claim 4 wherein $R_1$ and $R_2$ are both phenyl.

6. A process for the dehydroxylation of an alpha-hydroxyketone comprising:
   (a) reacting an alpha-hydroxyketone with a solution of lithium diphenylphosphide, said solution being of a concentration sufficient to react with both the hydroxy and the ketone moieties to form an intermediate capable of further reaction with an alkyliodide; and
   (b) adding an alkyliodide and an organic acid to the reaction mixture of step (a) to form the corresponding methylene ketone.

7. The process of claim 6 wherein the alpha-hydroxyketone is of the formula:

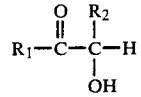

wherein $R_1$ and $R_2$ are the same or are different and are selected from the group consisting of a straight or branched chain alkyl having 1 to 10 carbon atoms, inclusive; cycloalkyl having 4 to 8 carbon atoms, inclusive; aryl and substituted aryl each having 6 to 12 ring carbon atoms, inclusive, wherein the substituents are selected from the group consisting of alkyl having 1 to 6 carbon atoms, inclusive, alkoxy having 1 to 6 carbon atoms, inclusive, and alkylene having 2 to 6 carbon atoms, inclusive; aromatic heterocyclic having 5 to 7 ring carbon atoms, inclusive, wherein the hetero-atom is selected from sulfur, nitrogen and oxygen; and $R_1$ and $R_2$ can together form a ring of up to 10 carbon atoms, inclusive, with the alpha-hydroxyketone moiety to which they are attached.

8. The process of claim 6 wherein $R_1$ and $R_2$ are both phenyl.

9. The process of claim 6 wherein the alkyliodide is methyliodide.

10. The process of claim 6 wherein the organic acid is acetic acid.

11. The process of claim 10 wherein $R_1$ and $R_2$ are both phenyl and the alkyliodide is methyliodide.

* * * * *